(12) United States Patent
Marrone et al.

(10) Patent No.: US 11,643,387 B2
(45) Date of Patent: May 9, 2023

(54) PROCESS FOR THE SYNTHESIS OF UREA

(71) Applicant: Casale SA, Lugano (CH)

(72) Inventors: Leonardo Marrone, Mercallo (IT); Paolo Bertini, Lugano (CH)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 17/628,124

(22) PCT Filed: Jun. 9, 2020

(86) PCT No.: PCT/EP2020/065970
§ 371 (c)(1),
(2) Date: Jan. 18, 2022

(87) PCT Pub. No.: WO2021/008783
PCT Pub. Date: Jan. 21, 2021

(65) Prior Publication Data
US 2022/0251033 A1    Aug. 11, 2022

(30) Foreign Application Priority Data

Jul. 18, 2019 (EP) ..................................... 19186881

(51) Int. Cl.
*C07C 273/04* (2006.01)
*C07D 251/60* (2006.01)
(Continued)

(52) U.S. Cl.
CPC .............. *C07C 273/04* (2013.01); *B01J 3/04* (2013.01); *B01J 19/2445* (2013.01); *C07D 251/60* (2013.01); *Y02P 20/582* (2015.11)

(58) Field of Classification Search
None
See application file for complete search history.

(56) References Cited

U.S. PATENT DOCUMENTS

| | | | | |
|---|---|---|---|---|
| 3,091,637 A | * | 5/1963 | Cook | .................... C07C 273/04 564/72 |
| 5,403,956 A | * | 4/1995 | Pagani | .................. C07C 273/04 564/72 |

(Continued)

FOREIGN PATENT DOCUMENTS

| | | |
|---|---|---|
| CN | 1083806 A | 3/1994 |
| EP | 0544056 B1 | 6/1993 |
| EP | 1716111 B1 | 11/2006 |

OTHER PUBLICATIONS

International Search Report dated Aug. 18, 2020 issued in connection with PCT/EP2020/065970.
(Continued)

*Primary Examiner* — Jennifer A Leung
(74) *Attorney, Agent, or Firm* — Akerman LLP

(57) ABSTRACT

A process for synthesis of urea from ammonia and carbon dioxide comprising the synthesis of urea in parallel in a first urea reactor (1) at a first urea synthesis pressure and in a second urea reactor (2) at a second and lower urea synthesis pressure; a stripping step of the reaction effluent of the first reactor, which is performed in a stripper (4) operating at a stripping pressure lower than the first urea synthesis pressure; the reaction effluent (21) of the second reactor (2) and the stripper liquid effluent (11) are sent to a recovery section (13) where a carbamate-containing recycle solution (17) is produced, and said recycle solution (17) is sent partly to said first reactor and partly to said second reactor.

24 Claims, 3 Drawing Sheets

(51) Int. Cl.
*B01J 3/04* (2006.01)
*B01J 19/24* (2006.01)

(56) References Cited

U.S. PATENT DOCUMENTS

| | | | |
|---|---|---|---|
| 6,150,555 A | 11/2000 | Pagani et al. | |
| 2006/0052637 A1* | 3/2006 | Porro | C07C 273/12 564/67 |
| 2017/0081297 A1* | 3/2017 | Bertini | B01J 10/00 |

OTHER PUBLICATIONS

Written Opinion of the International Searching Authority dated Aug. 18, 2020 issued in connection with PCT/EP2020/065970.
International Preliminary Report on Patentability dated Jul. 7, 2021 issued in connection with PCT/EP2020/065970.
Ullmann's Encyclopedia of Industrial Chemistry, Wiley-VCH Verlag, 2012.

* cited by examiner

PROCESS FOR THE SYNTHESIS OF UREA

CROSS-REFERENCE TO RELATED APPLICATIONS

This application is a national phase of PCT/EP2020/065970, filed Jun. 9, 2020, and claims priority to EP 19186881.9, filed Jul. 18, 2019, the entire contents of both of which are hereby incorporated by reference.

FIELD OF THE INVENTION

The invention relates to the field of urea production.

PRIOR ART

Urea is produced industrially by reacting $NH_3$ and $CO_2$ at high pressure according to the following equilibrium reactions:

$$2\ NH_3 + CO_2 \leftrightarrow \text{ammonium carbamate}$$

$$\text{Ammonium carbamate} \leftrightarrow \text{urea} + \text{water}.$$

Urea has several industrial uses including the production of fertilizers and the production of melamine. Melamine can be produced from urea with a low-pressure catalytic process or, preferably, with a high-pressure non-catalytic process. These processes for the synthesis of melamine are familiar to a skilled person.

The integration of a urea plant with a melamine plant is attractive because melamine is synthesized from urea and the melamine synthesis reaction releases offgas mainly composed of ammonia and carbon dioxide (melamine offgas) which can be recycled to the urea plant, either directly in gaseous form or after condensation.

According to the above reactions, the reaction effluent contains urea, water and unconverted reagents mostly in the form of ammonium carbamate. As the yield of the conversion is relatively low, the amount of ammonium carbamate (i.e. unconverted matter) in the effluent of a synthesis reactor is significant.

The ammonium carbamate contained in the reaction effluent can be neutralized to form by-products (once-through process) or recycled to the reactor (recycle process). In a recycle process, the ammonium carbamate is decomposed and the so obtained ammonia and carbon dioxide are recycled to the reactor, either in a gaseous state or after condensation, e.g. in the form of a carbamate-containing recycle solution. Decomposition of carbamate is obtained by heating the solution, typically with steam in a shell-and-tube apparatus. Therefore, the recovery section consumes energy in the form of hot steam.

An overview of different processes for the urea production can be found in literature, e.g. Ullmann's Encyclopedia of Industrial Chemistry, Wiley-VCH Verlag.

A known technique provides that synthesis of urea is performed in a primary reactor and a secondary reactor at different pressure.

EP 0 544 056 discloses a process wherein urea is synthesized mostly in a once-through primary reactor at a first pressure, and partly in a secondary reactor at a second pressure lower than the first pressure. The primary reactor receives all the fresh carbon dioxide feed and ammonia feed, possibly with some recycle ammonia to adjust the ammonia to carbon ratio, via a high pressure carbamate condenser. The vapour effluent of the primary reactor is sent to the secondary reactor together with a recycle solution produced in the recovery section. The liquid effluents of both reactors are sent to the downstream sections.

According to this scheme, the fresh reagents are fully sent to the primary reactor while the recycle solution is fully sent to the secondary reactor. The fresh reagents are condensed only partially in the above mentioned carbamate condenser because the heat balance of the reactor requires that a certain amount of reagents be in the gaseous state, particularly gaseous $CO_2$. The partial condensation in the carbamate condenser is normally regulated to maintain a target temperature in the reactor, e.g. 195 to 200° C.

An interesting feature is the recovery of heat of condensation from the high pressure carbamate condenser. Typically, the heat of condensation is transferred to a feed water to produce a low-pressure steam for a further use as a heat source in the process. For example, steam can be used in the recovery section for the thermal decomposition of carbamate, or in an evaporation section to remove water from the urea solution. In a urea-melamine plant, steam may be used among others in a melamine crystallization section.

The above described process has a good efficiency from the energetic point of view. However, the amount of heat exchanged in the high pressure carbamate condenser, and therefore the amount of steam that can be produced, is substantially dictated by the flow rate of fresh carbon dioxide sent to the primary reactor. The fresh gaseous carbon dioxide (from the battery limits) which is fed to the primary reactor determines the process of partial condensation and, consequently, the production of steam in the carbamate condenser.

The steam required by the process may change significantly, e.g. according to the kind of urea process and the presence of a tied-in melamine section. The fact that the heat recoverable from the carbamate condenser strongly depends on the amount of fresh carbon dioxide fed to the primary reactor can be a disadvantage in some cases, for example in the presence of a tied-in melamine plant. There is therefore the need to provide an even more flexible solution and to further reduce the consumption of energy.

CN 1083806 and U.S. Pat. No. 6,150,555 disclose a process where urea is produced in a first reaction space at 130 to 200 bar and in a once-through second reaction space at 250 to 450 bar.

SUMMARY OF THE INVENTION

The invention aims to improve the synthesis of urea involving two different reactors operating in parallel at different pressure. Particularly, the invention aims to obtain more flexibility and energy efficiency compared to the prior art.

The aims are reached with a process for synthesis of urea from ammonia and carbon dioxide comprising:

synthesis of urea in a first urea synthesis section including at least one first urea reactor, said first urea synthesis section operating at a first urea synthesis pressure and delivering a first reaction effluent containing urea;

synthesis of urea in a second urea synthesis section including at least one second urea reactor, said second urea synthesis section operating at a second urea synthesis pressure, which is lower than said first urea synthesis pressure, and delivering a second reaction effluent containing urea;

a stripping step of said first reaction effluent, which is performed in a stripping section including at least one stripper operating at a stripping pressure lower than the first synthesis pressure, obtaining a urea-containing liquid stripper effluent and a gaseous phase containing ammonia and carbon dioxide;

wherein said second reaction effluent and said stripper liquid effluent are sent to a recovery section where a carbamate-containing recycle solution is produced, and said recycle solution is sent partly to said first reactor and partly to said second reactor.

The first urea synthesis section and the second urea synthesis section normally comprise a single urea reactor each. However, in principle, either section may include several reactors in parallel. In the following description, references to a first reactor and second reactor shall include also embodiments with a plurality of first reactors or a plurality of second reactors.

Preferably the process comprises: sending the gaseous phase withdrawn from the stripper to a condenser and sending the condensate effluent of said condenser to said second reactor. The condenser can be termed a carbamate condenser and is located between the stripper and the second synthesis section.

The gaseous phase from the stripper may be condensed deliberately partially in the condenser, so that the condensate effluent is a biphasic stream still comprising ammonia and/or carbon dioxide in a gaseous state.

The invention uses a first urea reactor, which may be termed primary urea reactor, and a second urea reactor, which may be termed secondary reactor.

The primary reactor operates at a greater pressure and produces a greater amount of urea than the secondary reactor. More than one primary reactor and/or more than one secondary reactor may be provided, e.g. in parallel, if necessary.

The fresh reagents, namely ammonia and carbon dioxide, may be split between the first reactor and the second reactor. The fresh ammonia may be added with recycle ammonia to reach a target N/C ratio in the reactor.

Preferably the majority of the fresh $CO_2$ feed is sent to the first reactor. In a preferred embodiment, 80% or more of the fresh $CO_2$ feed is sent to the reactor.

A feature of the invention is that the recycle solution is sent to both the first and the second reactor, i.e. it is split between them. In a preferred embodiment, the majority of the recycle solution, more preferably 75% or more, is sent to the first reactor.

A particularly preferred embodiment provides that the first reactor receives the majority of the fresh $CO_2$ feed and also the majority of the recycle solution.

More preferably said first reactor receives at least 80% of the $CO_2$ feed and at least 75% of the recycle solution.

The majority of the urea is preferably synthesized in the first reactor. The total urea synthesized includes the urea contained in the stripper effluent (i.e. synthesized in the first reactor) and the urea contained in the second reactor effluent. Preferably the majority (i.e. more than 50%) of the total urea is synthesized in the first reactor. In other words, more than 50% of the total urea is contained in the stripper liquid effluent.

The gaseous phase withdrawn from the stripper has preferably an elevated nitrogen to carbon molar ratio, i.e. it is rich in nitrogen. Preferably said ratio in the gaseous phase from the stripper is 3.5 or is greater than 3.5.

The stripping step, which is performed on the effluent of the first reactor, is preferably a thermal stripping. The term of thermal stripping denotes a stripping process where the ammonium carbamate contained in the effluent is decomposed with heat, e.g. furnished by a hot steam, and without the addition of a gaseous stripping medium to the effluent.

Thermal stripping is performed, for example, with a shell-and-tube apparatus where the effluent is fed into the tubes and the shell side around the tubes is traversed by a hot medium, e.g. hot steam. The preferred embodiment of thermal stripping however is not limiting and a stripping process involving the addition of a stripping agent (e.g. gaseous ammonia or $CO_2$) may be used.

The first reactor operates at a pressure substantially greater than the second reactor. For example, the operating pressure of the first reactor is at least 10 bar greater, more preferably at least 20 bar greater, than the operating pressure of the second reactor. The first reactor operates preferably at a pressure of 200 bar or greater, preferably 200 to 300 bar and more preferably 220 to 240 bar. The second reactor operates preferably at a pressure of 120 to 180 bar, more preferably 140 to 160 bar. All pressures are relative to atmospheric pressure, i.e. they are given in bar gauge.

The first reactor operates preferably with a nitrogen to carbon (N/C) ratio of 3.5 to 4. The preferred hydrogen to carbon (H/C) ratio in the first reactor is 0.3 to 0.7.

In a preferred embodiment the at least one first reactor operates with N/C ratio in the range 3.5 to 4 and with H/C ratio in the range 0.3 to 0.7, and the at least one second reactor operates with N/C ratio in the range 3.3 to 3.8 and H/C ratio in the range 0.5 to 1.0.

Particularly preferably, the first reactor operates with N/C ratio of 3.7 and H/C ratio of 0.45. The second reactor operates preferably with N/C ratio of 3.4 and H/C ratio of 0.55.

The recovery section produces a urea solution which may contain around 70% urea and balance water, possibly with minor amounts of impurities. Part or all of the urea may be used to produce melamine. The production of melamine requires a highly concentrated or almost pure urea melt and therefore the solution may be concentrated in an evaporation section to remove water.

An aspect of the invention is also a plant according to the claims.

In some embodiments, the plant is an integrated urea-melamine plant including a urea section and a tied-in melamine section, wherein part or all of the urea synthesized in the urea section is used in the melamine section to produce melamine.

The invention may also be applied to revamping of urea plants.

For example a once-through urea plant may be revamped by: using the existing reactor, originally designed as once-through reactor, as the first reactor; installing the second reactor operating at a lower pressure. The other items of the plant, such as stripper and high-pressure condenser, may also be installed if necessary.

An important feature of the invention is stripping of the effluent of the first reactor, and sending the stripper vapours to the second reactor, possibly via a condenser (carbamate condenser). Accordingly, the carbamate condenser is moved to the feed line of the second reactor. The first reactor, on the other hand, receives a portion of the carbamate-containing recycle solution, being no longer operated according to the once-through process. An interesting advantage of the invention is to regulate the amount of recycle solution sent to the first reactor and second reactor. By varying the amount of this solution, the heat duty of the stripper is also controlled, as well as the heat that can be recovered in the carbamate condenser.

The invention provides an additional parameter for the control of the first reactor, namely the amount of recycle solution sent to said reactor. The steam that can be produced in the carbamate condenser, for use in the downstream equipment, is therefore less dependent on the regulation of the first reactor.

Another advantage is that the stripper vapours (i.e. gaseous phase withdrawn from top of the stripper) are rich in ammonia, to the benefit of the urea conversion.

The invention provides a process which is more flexible to combine an optimum conversion yield with the production of the required steam for the downstream equipment. Particularly, the invention allows producing steam on the basis of the need of the downstream processes (e.g. evaporation processes, integration with melamine plant) keeping optimum conditions for the urea synthesis reaction in the first reactor.

An interesting application of the invention is an integrated urea-melamine plant. In an integrated urea-melamine plant, the amount of recycle carbamate solution is normally greater than usual (e.g. than stand-alone urea plants) and gives more freedom for the regulation of the urea synthesis reactor, without affecting the heat which can be recovered in the carbamate condenser.

Still another advantage of the invention is a better energy efficiency. Urea can be produced with a lower energy input compared to the prior art, that means lower cost for the production.

DETAILED DESCRIPTION

Figure 1:
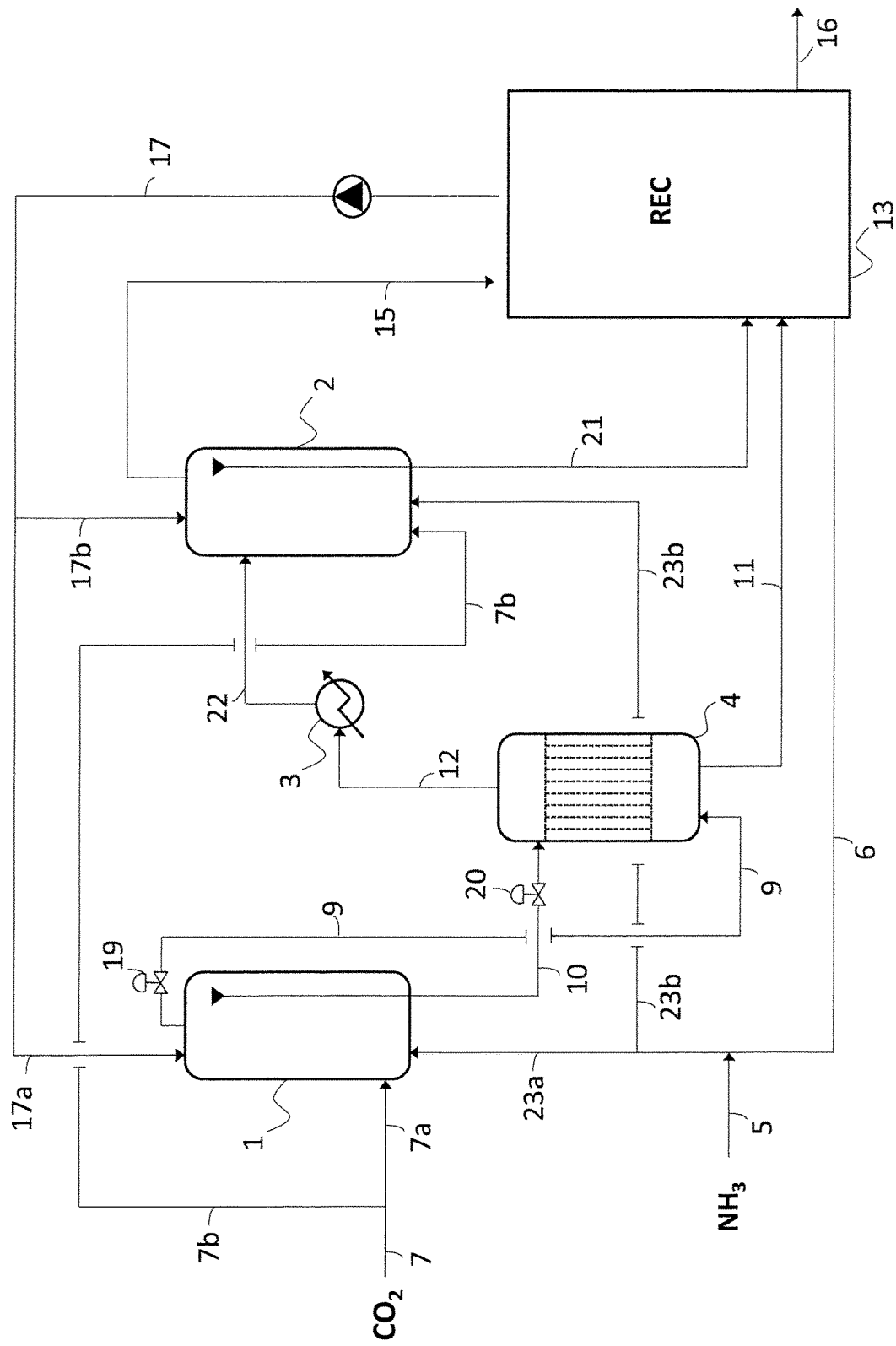
FIG. 1 is a scheme of a urea plant according to a first embodiment.

FIG. 1 illustrates basically a primary urea reactor 1, a secondary urea reactor 2, a carbamate condenser 3, a stripper 4, a recovery section (REC) 13.

The primary reactor 1 operates at a high pressure, for example 230 bar. The secondary reactor 2 operates also at a high pressure, although lower than the pressure of the reactor 1, for example 145 bar. Both reactors 1 and 2 are preferably realized as vertical vessels with suitable internals, e.g. perforated trays, to enhance the heat and mass transfer between the phases, and a downcomer pipe to collect the reaction effluent from top.

The recovery section 13 is realized according to known art and may comprise one or more recovery stages at different pressures lower than the reaction pressure in the reactors 1 and 2. For example the recovery section 13 may comprise a single stage at a low pressure or a first stage at medium pressure followed by a second stage at low pressure. A medium pressure is for example 2 to 10 bar while a low pressure is for example less than 2 bar and can be atmospheric pressure. The recovery stage or each recovery stage may comprise a carbamate decomposer and a condenser, according to known art.

The stripper 4 may operate at the same or a lower pressure than the primary reactor 1. Preferably the stripper 4 operates at a pressure equal or close to the pressure of the secondary reactor 2. The stripper 4 is for example a shell-end-tube apparatus with a bundle of tubes externally heated by hot steam (not shown).

A fresh ammonia feed 5, possibly added with recycle ammonia 6, is sent partly to the primary urea reactor 1 via line 23a and partly to the secondary urea reactor 2 via line 23b. The recycle ammonia 6 may be present in some embodiments of the invention, for example said recycle ammonia 6 comes from a medium-pressure recovery stage of the recovery section 13.

A fresh $CO_2$ feed 7 is sent partly to the primary urea reactor 1 via line 7a and partly to the secondary urea reactor 2 via line 7b.

The carbamate-containing recycle solution 17 from the recovery section 13 is sent partly to the primary urea reactor 1 via line 17a and partly to the secondary urea reactor 2 via line 17b.

The urea-containing effluent 10 from the primary reactor 1 is typically an aqueous solution of urea containing unreacted ammonia and carbon dioxide, mostly in the form of ammonium carbamate. This effluent 10 is sent to the tube side of the stripper 4 and depressurized by the valve 20.

In the tubes of the stripper 4, the solution 10 is heated in order to decompose the ammonium carbamate. As a result, a purified solution 11 and overhead gas 12 are obtained.

The purified solution 11 is sent to the recovery section 13 for further processing. The processing in the section 13 may include one or more decomposition steps at a medium or lower pressure as mentioned above. The recovery section 13 produces a purified urea solution 16, typically containing around 70% urea and balance water, and the recycle carbamate solution 17. Said solution 17 is pumped back to the reactors 1 and 2 via lines 17a and 17b.

In some embodiments, some or all the urea solution 16 can be used to produce melamine in a tied-in melamine synthesis plant and the melamine offgas are recycled to the urea plant. To this purpose, the urea solution 16 is concentrated e.g. by an evaporation section.

The stripper overhead vapours 12, which are predominantly composed of ammonia and carbon dioxide, are partially condensed in the carbamate condenser 3. The heat removed from said vapours 12 during their partial condensation is transferred, by indirect heat exchange, to a boiling water to produce steam. The steam so produced may be used elsewhere, e.g. in the recovery section 13 for the decomposition of carbamate still contained in the solution 11.

The effluent 22 of the carbamate condenser 3 is sent to the secondary reactor 2. Said effluent 22 is typically a biphasic stream due to the partial condensation. It shall be noted that the heat removed from the vapours 12 in the condenser 3 can regulate the temperature of the secondary reactor 2.

The urea-containing effluent solution 21 from the secondary reactor 2 is also sent to the recovery section 13 for further processing. Said solution 21 may be processed together with the solution 11 coming from the primary reactor 1.

FIG. 1 illustrates a preferred embodiment wherein the overhead gas 9 withdrawn from the primary reactor 1 is sent, via a regulation valve 19, to the bottom of the stripper 4 for passivation of the stripper. This overhead gas 9 typically contains some oxygen and is therefore effective as a passivation agent against corrosion.

The overhead gas 15 withdrawn from the top of the secondary reactor 2 can be sent to the recovery section 13 for condensation.

Some embodiments of the invention may not comprise the condenser 3, i.e. the stripper overhead gas 12 is sent directly to the secondary reactor 2 without a partial condensation. This embodiment without the partial condensation in the condenser 3 can be appropriate, in particular, when a large amount of recycle solution 17 is available, which is typically the case of a urea-melamine integrated plant. In such a case, the secondary reactor 2 is a relatively "cold" reactor and, consequently, it may be unnecessary to remove heat from the vapours 12 in the condenser 3. Therefore, embodiments without the condenser 3 can be contemplated.

The invention achieves the above mentioned aims. In particular, the partition of the recycle solution 17 between the primary reactor 1 and the secondary reactor 2, in combination with the partition of the $CO_2$ feed 7, allow a greater freedom in the regulation of the temperature of the reactors. For example, by increasing the fraction 17a directed to the primary reactor 1, the heat duty of the stripper 4 is increased and also the heat than can be recovered by the condenser 3 is increased.

The invention has also the advantage of an increased conversion efficiency with respect to the conventional technique of urea plants with two reactors in parallel, wherein the primary reactor is a once-through reactor. By introducing the stripping step of the effluent of the primary reactor, the invention reduces the heat input for the recovery section and increases efficiency, because part of the unconverted reagents contained in the effluent 10 are recovered at high pressure in the stripper 4.

Figure 2:
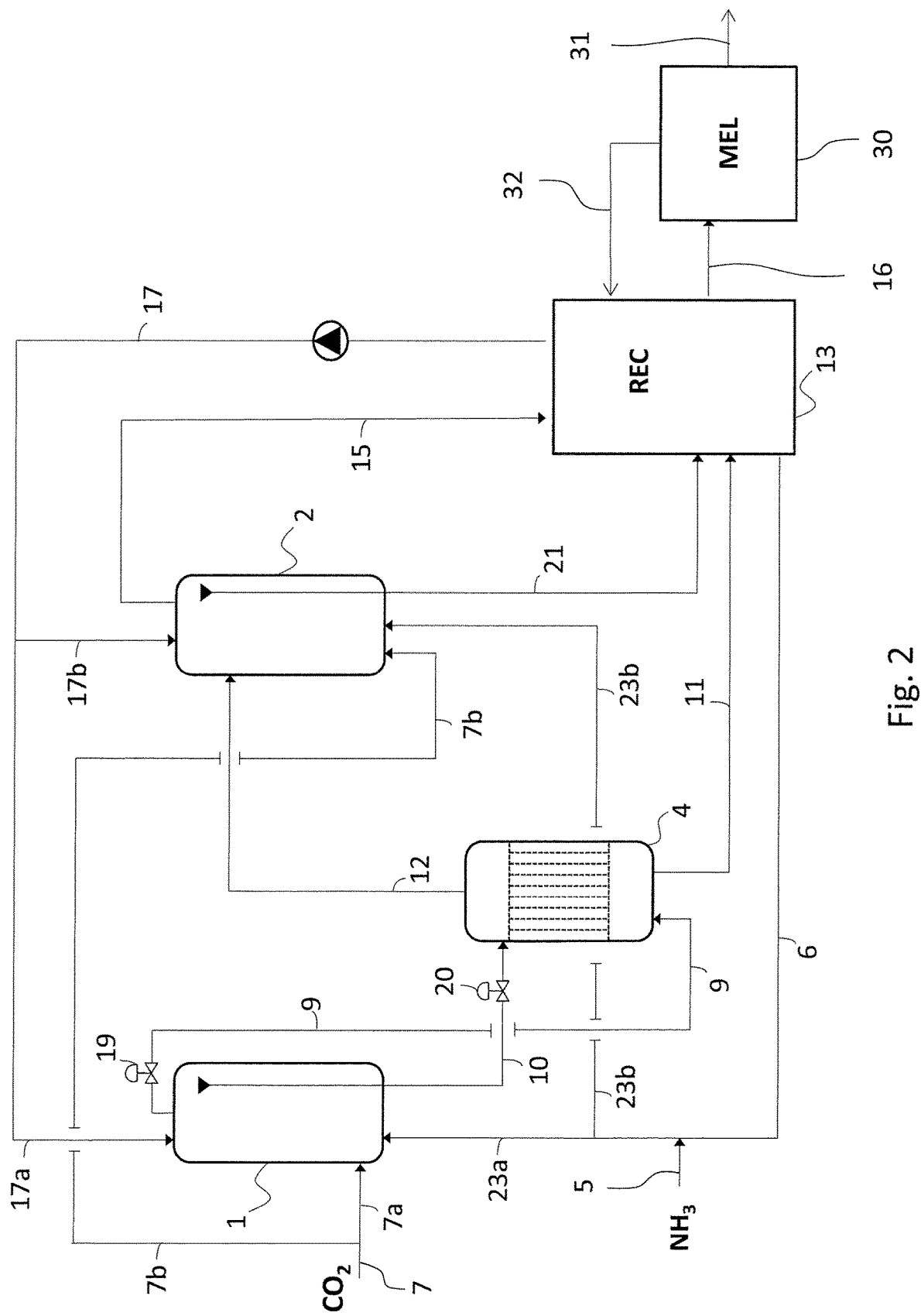
FIG. 2 is a scheme of a urea plant according to a second embodiment and with a tied-in melamine plant.

FIG. 2 illustrates an embodiment with a tied-in melamine plant (MEL) 30 wherein the urea solution 16 is used to produce melamine 31. To this purpose, the urea solution 16 is suitably concentrated (e.g. in an evaporation section) and converted into melamine according to a known process for the synthesis of melamine, preferably a non-catalytic high-pressure process.

The melamine plant 30 discharges melamine offgas 32 which are predominantly made of ammonia and carbon dioxide and are recycled to the urea synthesis plant. In the example of FIG. 2, the offgas 32 are condensed, at least partially, in the recovery section 13, so that the reagents are recycled to the urea reactors 1 and 2 via the carbamate solution 17. This embodiment may be preferred when the offgas 32 are discharged at a medium pressure which does not allow their direct introduction into the high-pressure urea synthesis section. The integration between the urea process and the melamine process, in the scheme of FIG. 2, can be made in accordance with EP 1 716 111.

FIG. 2 illustrates an embodiment without the carbamate condenser 3. Accordingly, the stripper overhead vapours 12 are sent directly into the secondary reactor 2. In a variant embodiment, however, the condenser 3 can be maintained.

Figure 3:
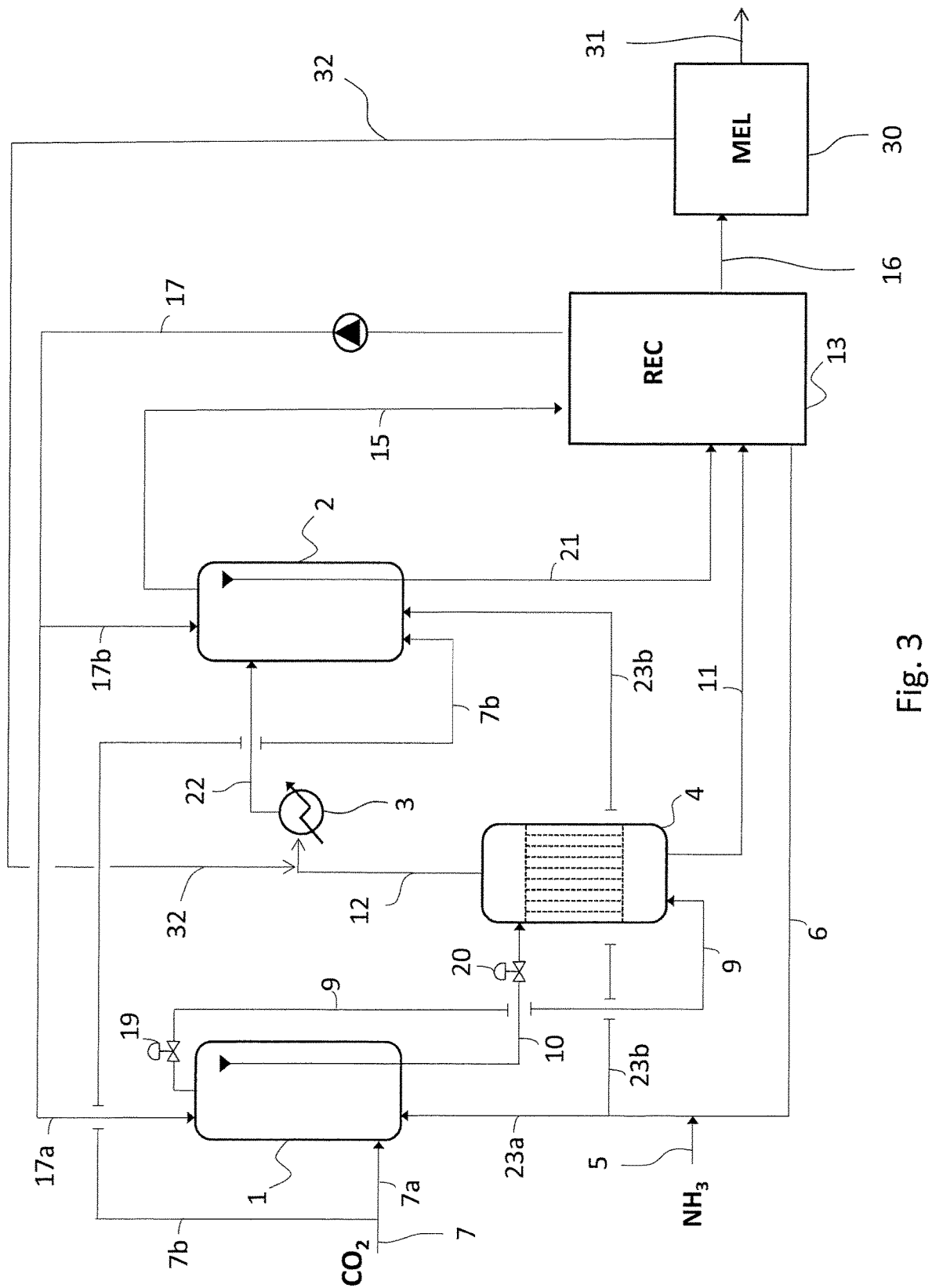
FIG. 3 is a scheme of a third embodiment.

FIG. 3 illustrates an embodiment wherein the offgas 32 of the melamine plant 30 are discharged at a high pressure. In this embodiment it can be possible and advantageous to send the melamine offgas 32 directly to the high-pressure carbamate condenser 3. Optionally, the melamine offgas 32 can be mixed with the stripper vapours 12 before introduction into said condenser 3, as shown.

EXAMPLE

The primary reactor 1 is operated at N/C=0.37 and H/C=0.45, 230 bar and 195° C. and receives 80% of the fresh $CO_2$ feed 7 and 75% of the recycle solution 17.

The remaining 20% of $CO_2$ and 25% of recycle solution are sent to the secondary reactor 2, which operates at N/C=3.4, H/C=0.55 and 145 bar.

The primary reactor 1 produces 75% of the total urea delivered to the recovery section 13 (i.e. urea contained in the streams 11 and 21) and the conversion rate (relative to $CO_2$ in the liquid phase) calculated for the liquid effluent 11 leaving the stripper 4 reaches 82%.

The remaining 25% of urea is produced in the secondary reactor 2 with a conversion rate of 60%. Therefore, the overall conversion rate is around 76%. A conventional plant with a once-through primary reactor, in similar conditions, has an overall conversion rate not exceeding 70%.

What is claimed is:

1. A process for synthesis of urea from ammonia and carbon dioxide comprising:
    synthesizing urea in a first urea synthesis section including at least one first urea reactor, said first urea synthesis section operating at a first urea synthesis pressure and delivering a first reaction effluent containing urea;
    synthesizing urea in a second urea synthesis section including at least one second urea reactor, said second urea synthesis section operating at a second urea synthesis pressure, which is lower than said first urea synthesis pressure, and delivering a second reaction effluent containing urea;
    stripping said first reaction effluent in a stripping section including at least one stripper operating at a stripping pressure lower than the first urea synthesis pressure to obtain a urea-containing liquid stripper effluent and a gaseous phase containing vapours of ammonia and carbon dioxide;
    sending said reaction effluent and said liquid stripper effluent to a recovery section to produce a carbamate-containing recycle solution, and
    sending said recycle solution partly to said at least one first urea reactor and partly to said at least one second urea reactor.

2. The process according to claim 1, comprising:
    sending the gaseous phase withdrawn from the stripping section to at least one carbamate condenser and sending a condensate effluent of said at least one carbamate condenser to said at least one second urea reactor.

3. The process according to claim 2, wherein the gaseous phase from the stripping section is condensed only partially, so that the condensate effluent is a biphasic stream still comprising ammonia and/or carbon dioxide in a gaseous state.

4. The process according to claim 1, comprising sending a first amount of a fresh ammonia feed to said at least one first urea reactor and sending a second amount of said fresh ammonia feed to said at least one second urea reactor, wherein said fresh ammonia feed is optionally mixed with a recycle ammonia obtained from the recovery section.

5. The process according to claim 1, comprising feeding a first amount of a fresh $CO_2$ feed to said at least one first urea reactor and feeding a second amount of said fresh $CO_2$ feed to said at least one second urea reactor.

6. The process according to claim 5, wherein a majority of the fresh $CO_2$ feed is sent to said at least one first urea reactor.

7. The process according to claim 1, wherein a majority of the recycle solution is sent to said at least one first urea reactor.

8. The process according to claim 6, wherein at least 80% of the fresh $CO_2$ feed and at least 75% of the recycle solution are sent to the at least one first urea reactor.

9. The process according to claim 1, wherein the majority of the urea collectively contained in the second reaction effluent and in the liquid stripper effluent is synthesized in the first urea synthesis section.

10. The process according to claim 1, wherein the gaseous phase withdrawn from the stripping section has a nitrogen to carbon molar ratio of 4 or greater.

11. The process according to claim 1, wherein the stripping step is a thermal stripping which is performed without the addition of a gaseous stripping medium.

12. The process according to claim 1, wherein the at least one first urea reactor operates at a pressure of 200 bar or greater.

13. The process according to claim 1, wherein the at least one second urea reactor operates at a pressure of 120 to 180 bar.

14. The process according to claim 1, wherein the at least one first urea reactor operates with nitrogen to carbon ratio of 3.5 to 4.

15. The process according to claim 14, wherein the at least one first urea reactor operates with hydrogen to carbon ratio of 0.3 to 0.7, and the at least one second urea reactor operates with nitrogen to carbon ratio of 3.3 to 3.8 and hydrogen to carbon ratio of 0.5 to 1.0.

16. The process according to claim 1, comprising synthesizing melamine using at least part of a urea solution produced by the recovery section.

17. A plant comprising:
a first urea synthesis section including at least one first urea reactor operated at a first synthesis pressure and where urea is synthesized from ammonia and carbon dioxide delivering a first reaction effluent containing urea;
a second urea synthesis section including at least one second urea reactor operated at a second synthesis pressure, which is lower than said first synthesis pressure, where urea is synthesized from ammonia and carbon dioxide delivering a second reaction effluent containing urea;
a stripper connected to the at least one first urea reactor to receive the first reaction effluent, wherein the stripper is operated at a stripping pressure lower than the first synthesis pressure, and the stripper delivers a urea-containing liquid effluent and a gaseous phase containing ammonia and carbon dioxide;
a recovery section;
means to feed the second reaction effluent and the urea-containing liquid effluent to said recovery section, and
means to feed a carbamate-containing recycle solution, which is produced in the recovery section, partly to said at least one first urea reactor and partly to said at least one second urea reactor.

18. The plant according to claim 17, comprising: at least one high-pressure condenser, means to send the gaseous phase from the stripper to said at least one high pressure condenser and means to send a condensate effluent of said at least one high-pressure condenser to said at least one second urea reactor.

19. The plant according to claim 17, wherein the plant is an integrated urea-melamine plant and includes a urea section including said first urea synthesis section, said second urea synthesis section, said stripper, said recovery section and said means to feed, and a tied-in melamine section, wherein part or all of the urea synthesized in the urea section is used in the melamine section to produce melamine.

20. The process according to claim 12, wherein the at least one first urea reactor operates at a pressure of 200 to 300 bar.

21. The process according to claim 12, wherein the at least one first urea reactor operates at a pressure of 220 to 240 bar.

22. The process according to claims 13, wherein the at least one second urea reactor operates at a pressure of 140 to 160 bar.

23. The process according to claim 6, wherein 80% or more of the fresh $CO_2$ feed is sent to said at least one first urea reactor.

24. The process according to claim 7, wherein 75% or more of the recycle solution is sent to said at least one first urea reactor.

* * * * *